US005602007A

United States Patent [19]
Dunn et al.

[11] Patent Number: 5,602,007
[45] Date of Patent: Feb. 11, 1997

[54] RECOMBINANT DNA MOLECULES

[75] Inventors: Ashley R. Dunn; Nicholas M. Gough, both of North Balwyn; Donald Metcalf, Balwyne, all of Australia

[73] Assignee: Research Corporation Technologies, Inc., Tucson, Ariz.

[21] Appl. No.: 283,108

[22] Filed: Dec. 9, 1988

Related U.S. Application Data

[63] Continuation of Ser. No. 708,765, Mar. 6, 1985, abandoned.

[30] Foreign Application Priority Data

Mar. 21, 1984 [AU] Australia .............................. PG4173/84

[51] Int. Cl.$^6$ ................... C12P 21/02; C12N 1/21; C12N 15/70
[52] U.S. Cl. ................... 435/69.5; 435/69.1; 435/91.1; 435/69.52; 435/172.3; 435/320.1; 435/252.3; 435/252.33; 536/23.51; 536/23.52; 514/2; 514/12; 935/4; 935/28; 935/37; 935/69; 935/11
[58] Field of Search ........................ 435/69.1, 91, 70.1, 435/70.3, 69.5, 69.52, 172.3, 320.1, 252.3, 252.33, 91.1; 935/4, 28, 37, 69, 11; 536/23.51, 23.52; 514/2, 12

[56] References Cited

U.S. PATENT DOCUMENTS

| | | | |
|---|---|---|---|
| 4,289,690 | 9/1981 | Pestka et al. | 530/351 |
| 4,438,032 | 3/1984 | Golde et al. | 260/172.2 |
| 4,658,018 | 4/1987 | Urdal et al. | 530/351 |
| 4,810,643 | 3/1989 | Souza | 435/69.5 |
| 5,298,603 | 3/1994 | Habermann et al. | 530/351 |

FOREIGN PATENT DOCUMENTS

WO86/00639 1/1986 WIPO.
WO86/03225 6/1986 WIPO.

OTHER PUBLICATIONS

Burgess, et al., 1977, *J. Biol. Chem.*, 252: 1998–2003.
Cantrell et al. (Sep. 1985) "Cloning, sequence and expression of a human granulocyte-macrophage colony stimulating factor", *Proc. Natl. Acad. Sci., USA* 82: 6250–6254.
Golde et al. (Dec. 1972) "Production of Colony–Simulating Factor By Human Macrophages", *The Lancet* 1397–1399.
Nicola et al. (Sep. 1979) "Separation of Functionally Distinct Human Granulocyte-Macrophage colony Stimulating Factors", *Blood* 54 (3):614–627.
Burgess et al. (Nov. 1982) "Colony–Forming Cell Proliferation: A Rapid and Sensitive Assay System for Murine Granulocyte–Macrophage Colony–Stimulating Factors", *Blood* 60 (5):1219–1223.
Wong et al. (May 1985) "Human GM–CSF: Molecular Cloning of the Complementary DNA and Purification of the Natural and Recombinant Proteins", *Science* 228:810–815.
Fung et al. (Jan. 1984) "Molecular Cloning of DNA for Murine Interleukin", *Nature* 307:233–236.

Hieter et al. (Nov. 1980) "Cloned Human and Mouse Kappa Immunoglobulin Constant and J Region Genes Conserve Homology in Functional Segments", *Cell* 22:197–207.
Yokota et al. (Feb. 1984) "Isolation and Characterization of a Mouse CDNA Clone that Expresses Mast–Cell Growth in a Factor Activity in Monkey Cells", *Proc. Natl. Acad. Sci., USA* 81:1070–1074.
Taniguchi et al. (Mar. 1983) "Structure and Expression of a Cloned CDNA for Human Interleukin–2", *Nature* 302:305–310.
Nicola et al. (Jul. 1978) "Preparation of Colony Stimulating Factors from Human Placental Conditioned Medium", *Leukemia Res.* 2 (14):313–322.
Miller et al. (1983) "Methods utilizing cell–free protein–synthesizing systems for the identification of recombinant DNA molecules", *Meth. Enzymol* 101:650–674.
Stanley et al. (Jun. 1977) "Factors regulating macrophage production and growth", *J. Biol. Chem.* 252:4305–4312.
Grunstein et al. (Oct. 1975) "Colony hybridization: A method for the isolation of cloned DNAs that contain a specific gene", *Proc. Natl. Acad. Sci., USA* 72:(10) 3961–3965.
Kaushansky et al. (May 1986) "Genomic cloning, characterization and multilineage growth–promoting activity of human granulocyte–macrophage colony–stimulating factor", *Proc. Natl. Acad. Sci., USA* 83: 3101–3105.
Cosman et al. (Dec. 1984) "Cloning sequence and expression of human interleukin–2 receptor", *Nature* 312:768–771.
Marquardt et al. (Aug. 1983) "Transforming Growth factors produced by retrovirus–transformed rodent fibroblasts and human melanoma cells: Amino acid sequence homology with epidermal growth factor", *Proc. Natl. Acad. Sci., USA* 80:4684–4688.
Moonen et al. (Jul. 1987) "Increased biological activity of deglycosylated recombinant human granulocyte/macrophage colony–stimulating factor produced by yeast or animal cells", *Proc. Natl. Acad. Sci., USA* 84: 4428–4431.
Lusis et al. (Sep. 1980) "Action of granulocyte–macrophage colony–stimulating factors: studies using a human leukemia cell line", *Proc. Natl. Acad. Sci., USA* 77 (9): 5346–5350.
Metcalf D. (Nov. 1988) "The granulocyte–macrophage colony stimulating factors", *Cell* 43: 5–6.

(List continued on next page.)

*Primary Examiner*—Christopher S. F. Low
*Attorney, Agent, or Firm*—Scully, Scott, Murphy & Presser

[57] ABSTRACT

This invention provides a DNA sequence coding for a mammalian granulocyte macrophage colony stimulating factor (GM-CSF), a method of obtaining same, vectors and hosts harboring same. The sequence is useful as a probe for identifying related sequences, selecting GM-CSF encoding mRNA from a mixture of mRNAs containing same, and a source of GM-CSF DNA for expression in an appropriate expression vector. The GM-CSF protein encoded by the sequence is useful for stimulating the production of granulocytes and macrophages from their respective progenitor cells.

31 Claims, 7 Drawing Sheets

OTHER PUBLICATIONS

Lee et al. (Jul. 1985) "Isolation of cDNA for a human granulocyte–macrophage colony–stimulating factor by functional expression in mammalian cells", *Proc. Natl. Acad. Sci. USA* 82 :4360–4364.

Lusis et al. (Jan. 1981) "Purification and characterization of a human T–lymphocyte–derived granulocyte–macrophage colony–stimulating factor", *Blood* 57(1): 13–21.

Watson et al 1987, in: *Molecular Biology of the Gene.* Benjamin/Cummings Publishing Co., Menlo Park, CA. p. 313.

Gough et al. 1984. Nature 309, 763–767.

Bleackley et al. 1983. Nuc. Acids Res. 11, 3027–3034.

Lusis et al. 1982. Nature 298, 75–77.

Maniatis et al. 1982. in: *Molecular Cloning: A Laboratory Manual.* Cold Spring Harbor Laboratory, Cold Spring Harbor, NY, pp. 404–406, 411–413, and 433.

```
         7    His                              16
      TrpLysCysValGluAlaIleLysGluAla           PROTEIN

5' TGGAAACATGTTGAAGCTATTAAAGAAGC 3'        mRNA
            G   C    C   G   C    C   G  G
                A        A       A
            TGT      G        G
            C

3' ACCTTTGTACACCTTCG 5'
            C   G    T   C
                A                             PROBE 1
                G

3' ACCTTTACACAACTTCG 5'
            C   G   G   C                     PROBE 2
                T
                C

3' CTTCGATAATTTCTTCG 5'
                C   G   G   C   C             PROBE 3
                        T

3' CTTCGTTAATTTCTTCG 5'
                C   C   G   C   C             PROBE 4
                        T
```

```
        ? Thr - Glu - - - - - - - - - - - - - - - Thr
       IleIleValThrArgProTrpLysHisValGluAlaIleLysGluAlaLeuAsnLeuLeu   20
       ATAATTGTTACCCGGCCTTGGAAGCATGTAGAGGCCATCAAAGAAGCCCTAAACCTCCTG   60

- - - Ser - - - - -
       AspAspMetProValThrLeuAsnGluGluValGluValValSerAsnGluPheSerPhe   40
       GATGACATGCCTGTCACGTTGAATGAAGAGGTAGAAGTCGTCTCTAACGAGTTCTCCTTC  120

***
       LysLysLeuThrCysValGlnThrArgLeuLysIlePheGluGlnGlyLeuArgGlyAsn   60
       AAGAAGCTAACATGTGTGCAGACCCGCCTGAAGATATTCGAGCAGGGTCTACGGGGCAAT  180

***
       PheThrLysLeuLysGlyAlaLeuAsnMetThrAlaSerTyrTyrGlnThrTyrCysPro   80
       TTCACCAAACTCAAGGGCGCCTTGAACATGACAGCCAGCTACTACCAGACATACTGCCCC  240
                                                              T

ProThrProGluThrAspCysGluThrGlnValThrThrTyrAlaAspPheIleAspSer  100
       CCAACTCCGGAAACGGACTGTGAAACACAAGTTACCACCTATGCGGATTTCATAGACAGC  300

Gly
       LeuLysThrPheLeuThrAspIleProPheGluCysLysLysProSerGlnLysTER    118
       CTTAAAACCTTTCTGACTGATATCCCCTTTGAATGCAAAAAACCAAGCCAAAAATGAGGA  360
                                                                G

AGCCCAGGCCAGCTCTGAATCCAGCTTCTCAGACTGCTGCTTTTGTGCCTGCGTAATGAG  420

CCAAGAACTTGGAATTTCTGCCTTAAAGGGACCAAGAGATGTGGCACAGCCACAGTTGGA  480

AGGCAGTATAGCCCTCTGAAAACGCTAACTCAGCTTGGACAGCGGAAGACAAACGAGAGA  540
                                                                G

TATTTTCTACTGATAGGGACCATTATATTTATTTATATATTTATATTTTTTAAATATTAT  600

TTATTTATTTATTTATTTTTGCAACTCTATTTATTGAGAATGTCTTACCAGAATAATAAA  660

TTATTAAAACTTTAAAAAAAAAAAAAAAAAAAA
```

FIG.7

RECOMBINANT DNA MOLECULES

This is a continuation of application Ser. No. 708,765, filed on Mar. 6, 1985, now abandoned.

FIELD OF THE INVENTION

This invention relates to DNA sequences, recombinant DNA molecules and processes for producing proteins or polypeptides with the specificity of protein molecules which control the production of particular blood cells. More specifically, this invention relates to DNA sequences and recombinant DNA molecules that are characterized in that they code for or include fragments that code for the protein molecule known as granulocyte-macrophage colony stimulating factor (GM-CSF).

BACKGROUND OF THE INVENTION

The production of blood cells such as erythrocytes (red blood cells), granulocytes, macrophages and lymphocytes is under the control of a set of protein molecules which stimulate multipotential precursor or stem cells in the bone marrow. During hematopoietic development, these multipotential cells form cells of limited developmental potential which are variously referred to as committed progenitor cells, colony forming cells or CFCs for individual blood cell types. Although there may be non-specific stimulators of the precursor stem cells or CFCs such as the so-called multi-CSF (interleukin-3) as described by Fung, M. C., et al., (*Nature* 307: 233–237(1984) or Yokota, T., et al., *Proc. Nat'l. Acad. Sci. USA* 81: 1070–1074 (1984)), there are specific regulators for each of the different cell lineages. In particular, the production of granulocytes and macrophages from their respective CFCs is under the control of glycoproteins such as granulocyte-macrophage colony stimulating factor (GM-CSF) as described by Burgess, A. W. et al., (*J. Biol. Chem.* 252: 1998–2003 (1977)), granulocyte colony stimulating factor (G-CSF) as described by Stanley, E. R. and Heard P. M., (*J. Biol. Chem.* 252: 4305–4312 (1977)) and macrophage colony stimulating factor (M-CSF) as described by Nicola, N. A. et al., (*J. Biol. Chem.* 258: 9017–9021 (1983)). Although these glycoproteins are of low abundance in the body, it has been possible to purify small amounts of the murine GM-CSF for partial amino acid sequence analysis and biological characterization.

However, unless an alternative source of these proteins can be found, these small amounts will be insufficient for clinical applications. If, however, these colony stimulating factors can be produced chemically or biosynthetically, it should be possible to use these factors to improve blood cell production in vivo, to produce blood cells in the laboratory for transfusion and to accelerate the maturation of leukemic cells. For each of these applications, it is imperative that the types of blood cells produced be restricted. In particular, it is important to limit the production or activation of lymphocytes and/or their precursors. Thus, whilst molecules such as multi-CSF could find application in some diseases where a general increase in blood cell production is required, the use of glycoproteins such as GM-CSF, G-CSF and M-CSF will be of particular importance since these stimulate only the production of cells required to fight primary infection or remove damaged tissue.

BRIEF DESCRIPTION OF THE INVENTION

This invention provides a DNA sequence coding for mammalian granulocyte-macrophage colony stimulating factor (GM-CSF) or its single or multiple base substitutions, deletions, insertions, or inversions, wherein said DNA sequence is derived from natural, synthetic or semi-synthetic sources and is capable of selectings via hybrid selection, an mRNA species capable of directing the synthesis of GM-CSF in vitro from a mixture of mRNAs containing same.

In another embodiment this invention provides a method of producing the DNA sequence coding for GM-CSF of comprising the steps of:

(a) preparing a source of mRNA containing GM-CSF mRNA;

(b) synthesizing duplex DNA copies of said source mRNA;

(c) cloning said DNA copies;

(d) providing synthetic GM-CSF probes;

(e) screening clones harboring the DNA copies of step (b) by colony hybridization with the probes of step (d);

(f) and recovering the clones which hybridized with said probes.

In another embodiment this invention provides a cloning vector comprising, in recombinant form, a DNA sequence having protein encoding portion whose code sequence has substantially one-to-one correspondence with granulocyte-macrophage colony stimulating factor (GM-CSF).

In another embodiment this invention provides a method of producing granulocyte-macrophage colony stimulating factor (GM-CSF) comprising culturing a host cell transformed by an expression vector comprising a promoter fragment which functions in said host and a DNA segment coding for GM-CSF, the DNA segment being in an orientation with said promoter such that in the host the GM-CSF DNA is expressed as a non-native CM-CSF protein.

In a final embodiment this invention provides a method for stimulating the production of granulocytes and macrophages comprising contacting respective progenitor cells of said granulocytes and macrophages with a stimulating effective amount of granulocyte-macrophage stimulating factor.

DETAILED DESCRIPTION OF THE DRAWINGS

FIG. 2(b) shows the nucleotide sequence of GM-CSF mRNA and predicted amino acid sequence of GM-CSF. The nucleotide sequence given is a composite of sequence derived from clones pGM37 and pGM38; at three positions where the pGM37 nucleotide sequence differs from that of pGM38 and pGM37 alternatives are given below the line. The sequence of the mRNA-synonymous strand is listed 5' to 3', with the predicted amino acid sequence of GM-CSF given above; numbers at the ends of lines indicate the position of the final residue (amino acid or nucleotide) on that line. The partial amino acid sequence determined for GM-CSF is indicated above the sequence derived from the clones; at positions where there is no discordance between the two, dashes are given. The first amino acid residue, determined by analysis of the protein, could not be assigned, and is indicated by a question mark.

DETAILED DESCRIPTION OF THE INVENTION

The present invention relates to the production and characterization of a recombinant DNA molecule for the production of the specific blood cell regulator granulocyte-macrophage colony stimulating factor (GM-CSF). In particular, this invention involves the production of DNA molecule coding for murine GM-CSF which may prove to be of particular importance in providing the basis for production of GM-CSF in alternative hosts, such as bacteria and animal cells. By way of example, the DNA molecule of this invention may be used as a probe to isolate the gene sequence for the eguivalent human GM-CSF for use in the production of human granulocytes and macrophages.

Figure 2A:
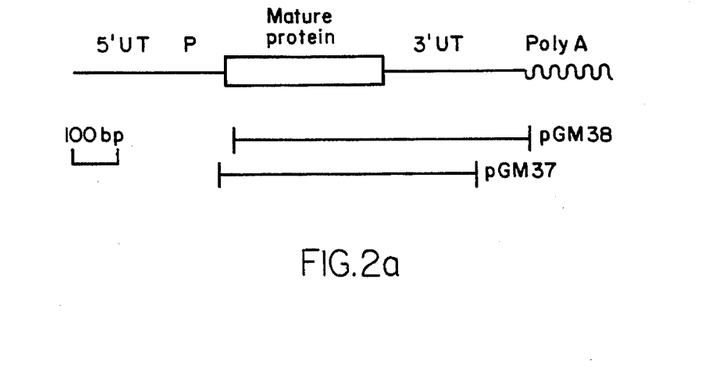
FIG. 2(a) shows a map of the GM-CSF mRNA and of clones pGM37 and pGM38. The mRNA is taken to be 1,200 nucleotides in length. The region of the mRNA encoding the mature protein is shown as a thick line. The untranslated regions are designated by UT and a putative precursor peptide by P. The regions contained within clones pGM37 and pGM38 are indicated with bars. pGM38 extends from nucleotide 14 in the sequence presented in FIG.(b) to the poly(A) tail, whereas pGM37 extends from 20 nucleotides 5' to the sequence presented to position 574.
Figure 2B:
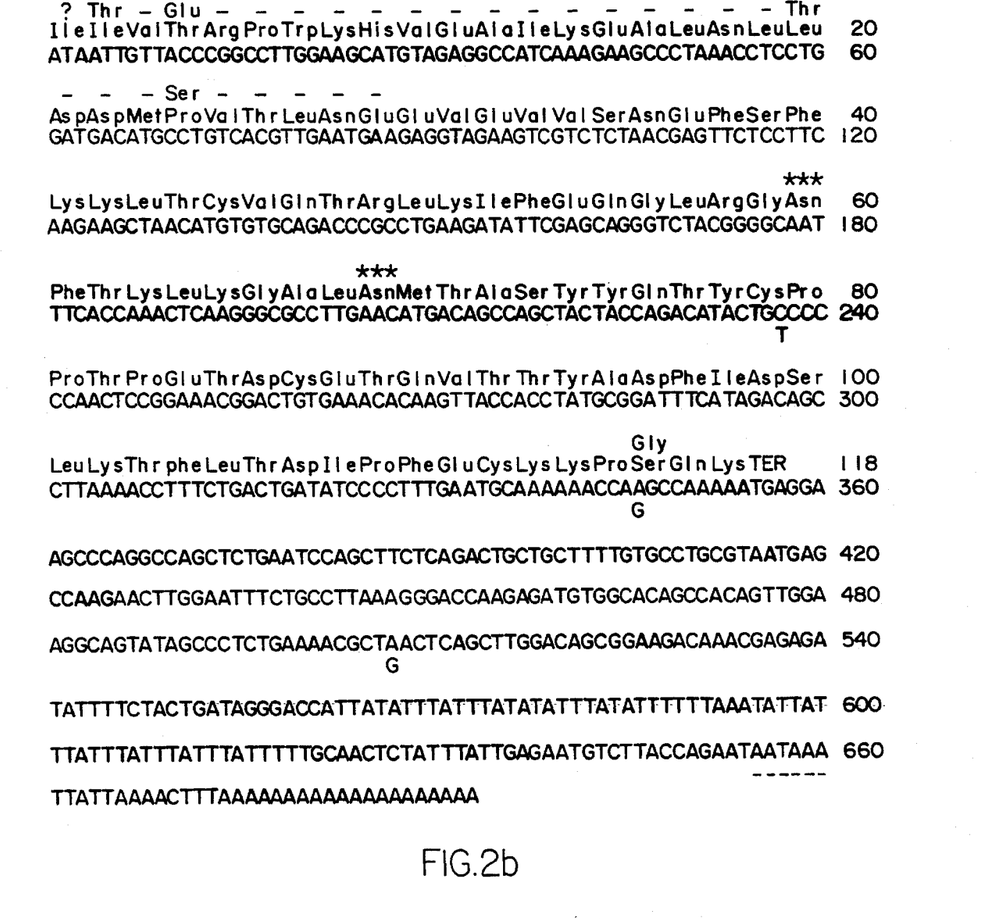

In one embodiment, the present invention provides a DNA sequence characterized in that at least a portion thereof codes for a protein or polypeptide displaying the biological activity of murine GM-CSF. A specific nucleotide sequence of this aspect of the invention is shown in FIG. 2 (b).

Clones harboring a nucleotide sequence useful for practicing the subject invention may be obtained by the following cloning strategy.

Isolation of a Murine GM-CSF cDNA Clone

One of the best sources of GM-CSF is stimulated mouse lung. A library of greater than $10^5$ cDNA clones complementary to lung mRNA from endotoxin-treated mice was constructed as detailed in Example I.

Figure 1:
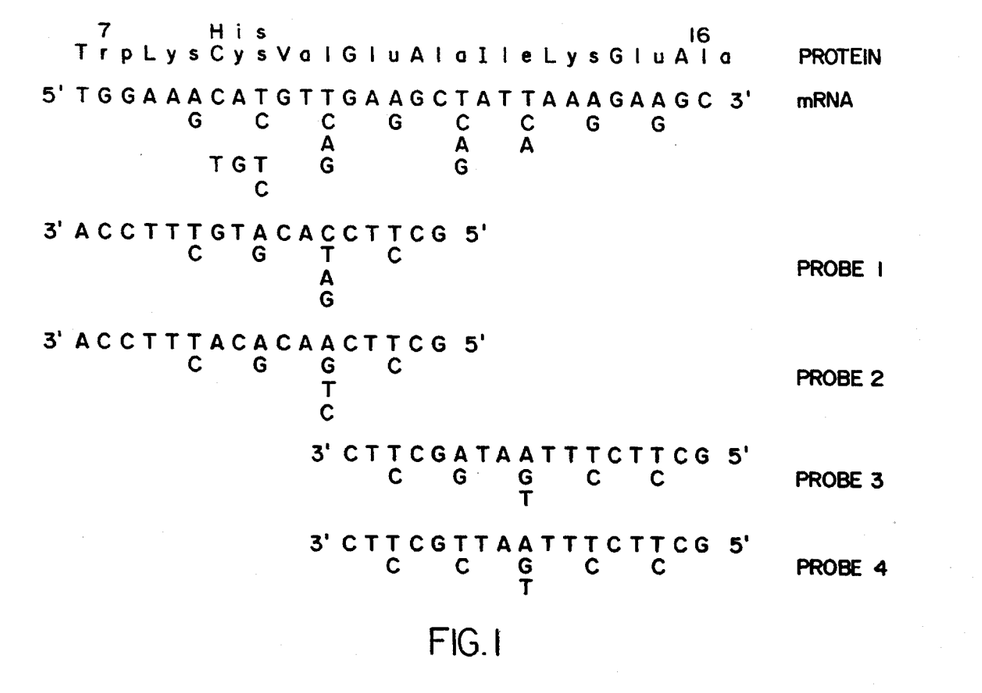
FIG. 1 shows the synthetic oligonucleotides used for identifying GM-CSF clones. A portion of the amino acid sequence of murine GM-CSF (residues 7-16) is shown on the top line, the possible combinations of nucleotide (mRNA) sequences that could encode this peptide segment in the middle, and the four different sets of oligonucleotide probes complementary to regions of the mRNA sequences below.

GM-CSF CDNA-containing recombinants were identified in this library using as probes, short synthetic oligonucleotides complementary to two portions of the GM-CSF mRNA sequence, as predicted from the partial amino acid sequences of the protein. FIG. 1 shows the region of the GM-CSF amino acid sequence between residues 7 and 16, the possible combinations of nucleotide sequences that could encode this peptide and the oligonucleotides that were used as hybridization probes. Since the assignment of amino acid residue 9 was equivocal (being either histidine or cysteine) two different sets of oligonucleotides encompassing this region were synthesized; probe 1 assumes a histidine residue and probe 2 a cysteine residue at position 9. The second region within the amino acid sequence required an extremely degenerate set of oligonucleotides which were synthesized as two 48-fold degenerate sets, (probes 3 and 4).

In order to identify GM-CSF recombinants a colony hybridization assay was employed. The library of cDNA clones was grown as single colonies on agar plates, replicas of the colonies transferred to nitrocellulose filters on which the colonies were then lysed and the plasmid DNA immobilized in situ. These filters were screened by hybridization with a mixture of all of the synthesized oligonucleotide probes which had been $^{32}$P-labelled.

After hybridization and washing the filters, colonies that had hybridized with the probes were identified by autoradiography. By this means, 22 independent recombinants that hybridized with the mixture of probes were identified. Whilst some of these may well represent irrelevant sequences (i.e., non-GM-CSF encoding sequences), with fortuitous homology with one of the oligonucleotides, it is unlikely that an irrelevant sequence will hybridize with two different probes independently, whereas the authentic GM-CSF sequence should hybridize with both probes 3/4 and either 1 or 2. Therefore, plasmid DNA from each of the 22 clones was isolated and electrophoresed on triplicate agarose gels. After the DNA was transferred to nitrocellulose by the Southern technique (*J. Mol. Biol.* 98: 503, (1975)), the three filters were hybridized with the three different probes independently. Of the 22 clones examined, 2 (clones 37 and 38) hybridized with both probes 1 and 3/4 and thus represented strong candidates for being GM-CSF DNA.

Confirmation of Identity of Clone

Two lines of experimentation demonstrated that clones 37 and 38 do in fact correspond to the GM-CSF gene sequence. Firstly, the nucleotide sequence of the clones was determined and is shown in FIG. 2 (b), along with its encoded amino acid sequence. The amino acid sequence predicted by the nucleotide sequence of the clones are substantially similar to the N-terminal amino acid sequence determined from analysis of the protein, there being only 4 discrepancies between the two out of 29 positions compared. Two of the discrepancies occur at positions which were only tentatively assigned in the protein sequence. Furthermore, the nucleotide sequence of the clone predicts a peptide with a molecular weight (13,500 daltons) very close to that expected for the GM-CSF protein.

Secondly, clone 38 can specifically select biologically active GM-CSF mRNA. Clone 38 DNA (and also DNA from the parental plasmid pJL3) was immobilized on nitrocellulose and was hybridized with RNA from mouse lung and also from a T cell line (LB3) which makes GM-CSF and a related (but distinct) regulator, IL3, after the cells have been stimulated with conA. After hybridization, the filters were washed to remove non-hybridized RNA and the specifically hybridized RNA then eluted. This RNA was injected into Xenopus oocytes (the ability of which to translate exogenous mRNA has been well documented) and the culture media assayed 3–5 days later for the presence of GM-CSF and IL3. The results of several experiments demonstrated that: (a) the vector DNA alone does not select GM-CSF mRNA; (b) clone 38 DNA selects GM-CSF mRNA from both lung RNA and from LB3; and (c) clone 38 does not select IL3 mRNA from LB3 RNA—an internal control of specificity (See Example II).

A third line of experiments provides strong additional support for the identity of clone 38. When used as a hybridization probe in a Northern blotting experiment, clone 38 detects an mRNA species of approximately 1.2 kb in length in RNA from cells which synthesize GM-CSF (mouse lung and conA-stimulated LB3) but not in a range of myeloid of lymphoid cells which do not synthesize GM-CSF nor in RNA from LB3 cells which had not been conA-stimulated. Thus, in the case of LB3, the mRNA corresponding to clone 38 is inducible along with the GM-CSF protein (See Example III).

Deposit of Strains Useful in Practicing the Invention

A deposit of a biologically pure culture of the following strains was made with the American Type Culture Collection, 12301 Parklawn Drive, Rockville, Md. on Feb. 21, 1985 the accession number indicated was assigned after successful viability testing, and the requisite fees were paid. Access to said culture will be available during pendency of the patent application to one determined by the Commissioner to be entitled thereto under 37 C.F.R. §1.14 and 35 U.S.C. §122. All restriction on availability of said culture to the public will be irrevocably removed upon the granting of a patent based upon the application and said culture will remain permanently available for a term of at least five years after the most recent request for the furnishing of a sample and in any case for a period of at least 30 years after the date of the deposit. Should the culture become nonviable or be inadvertently destroyed, it will be replaced with a viable culture(s) of the same taxonomic description.

| Strain/Plasmid | ATCC No. |
| --- | --- |
| pGM37 | 53032 |
| pGM38 | 53036 |

Utility of pGM37 and pGM38

In addition to providing a convenient source of clonable gentic information for murine GM-CSF the hybrid DNA molecules disclosed herein are also useful as probes for the detection and isolation of related gene sequences from other mammalian DNA libraries. In their use for the detection of related gene sequences, the probes are conveniently labelled with an analytically detectable reagent. The invention, however, should not be limited to any particular means of labelling. Although the examples employ a radioactive label for detection, other detection methods are well-known in the art and may be easily substituted. Alternative systems, although not limiting would include biotin-avidin, fluorescent dyes, protein, immunological assays such as ELISA where antibodies to derivitized probe molecules are used, or antibodies to DNA-DNA hybrids themselves are used; and assays wherein one strand of DNA is labelled with an inactive subunit of an enzyme and the probe is labelled with a second inactive subunit such that upon hybridization the subunits reassociate and enzyme activity is restored.

The cloned sequence may be subcloned into expression vectors. In situations where the gene sequence may be missing a partial sequence, such a sequence may be synthesized chemically, ligated to cloned sequence and introduced into an expression vector. The choice of an appropriate expression vector is well within the skill of an artisan in the field. Minimally, the expression vector will contain a promoter fragment which functions in the host to be transformed and a convenient endonuclease cleavage site such that the gene sequence coding for GM-CSF may be combined therewith.

EXAMPLE I

This Example demonstrates the isolation cDNA GM-CSF clones useful for practicing the subject invention.

Isolation of Mouse Lung mRNA

90 C57 BL/6 mice were injected with bacterial endotoxin (5 ug/mouse). After 3 hours the lungs were removed and incubated in vitro in serum free-Dulbecco's modified Eagles medium (Sheridan J. & D. Metcalf *J. Cell Physiol.* 81: 11–24 (1973)). After 0, 5 and 15 hours in vitro, batches of 30 pairs of lungs were homogenized for 60 seconds in 150 ml M Tris pH 7.5, M NaCl, M EDTA, 0.5% SDS, 200 ug/ml proteinase K. After incubation at 37° C. for 1 hour, the homogenate was mixed with an equal volume of 7M urea, 0.35M NaCl, 10 mM EDTA, 1% SDS, 10 mM Tris Cl (pH 7.4) and then extracted with phenol/chloroform/isoamylalcohol. RNA was precipitated from the aqueous phase by addition of ethanol. Poly $A^+$ RNA was selected from the total RNA by two rounds of chromatography on oligo-dT cellulose. The RNA prepared from the three different times of in vitro culture were pooled.

Synthesis and Construction of cDNA Clones

Figure 3:
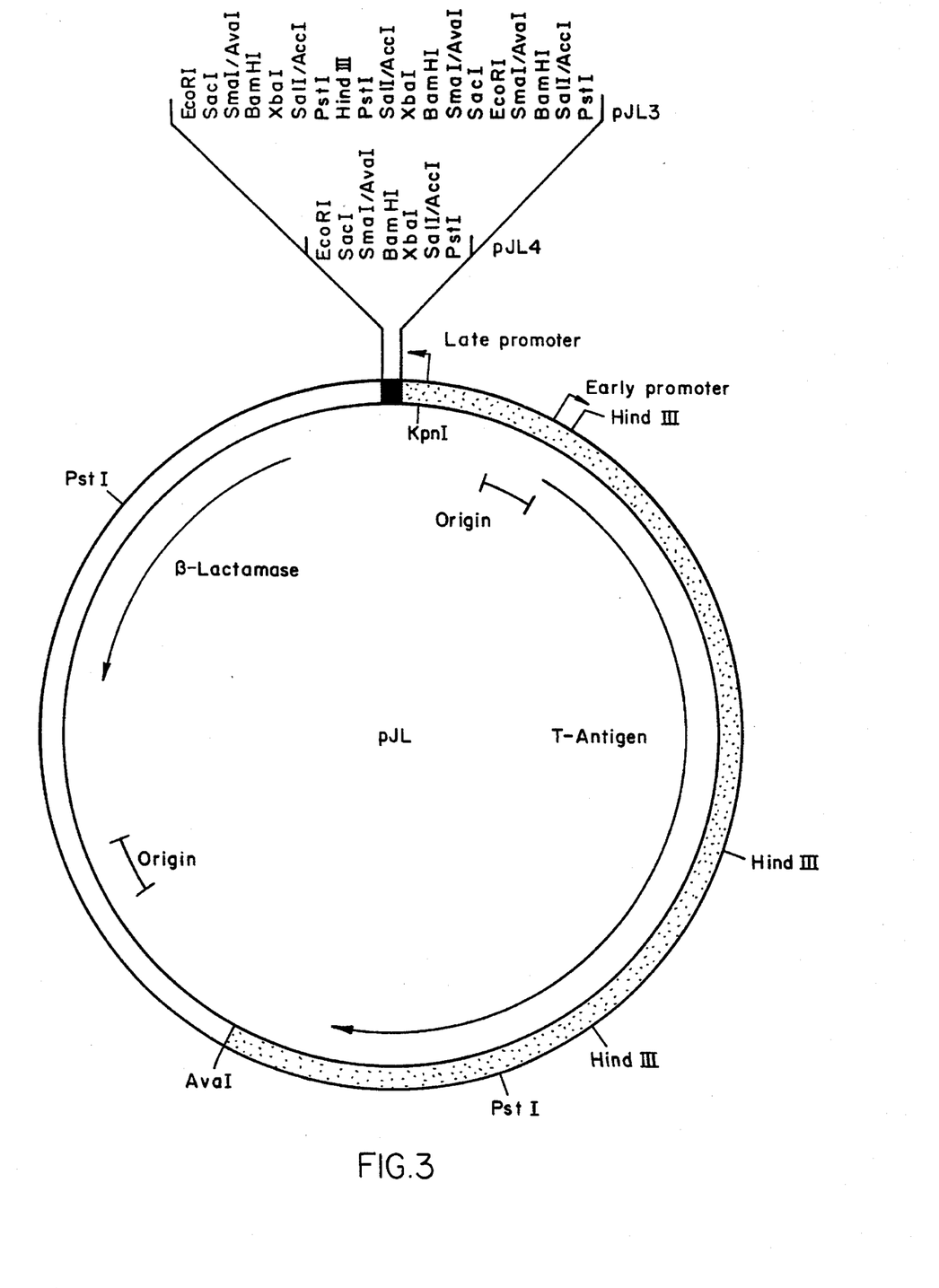
FIG. 3 shows a map of vector pJL3. The SV40-drived portion is shown as a thick line, and that derived from plasmid pAT153 as a thin line. The multicloning site is indicated at the top. Numbers given refer to the sequence of the parental SV40 or pAT153 sequences.

Duplex DNA copies of the pooled lung mRNA were synthesized using avian myeloblastosis virus reverse transcriptase for synthesis of the first-strand and *Escherichia coli* DNA polymerase I (Klenow fragment) for synthesis of the second strand, using standard techniques (Efstratiodas, A. et al. cell 7:279–288 (1976) and Maniatis, T., et al. "Molecular Cloning", Cold Spring Harbor Lab, N.Y. (1982)). After cleavage of the hairpin loop with $S_1$ nuclease, oligo(dC) tails (approximately 20–30 residues per end) were added using terminal deoxynucleotidyltransferase (Michelson, A. M. & S. Orkin *J. Biol. Chem.* 257: 14773–14782 (1982)). The tailed cDNA was fractionated by electrophoresis on a 1.5% agarose gel and molecules greater than 500 bases in length recovered and annealed to dG-tailed plasmid DNA. The plasmid used (pJL3) is an SV40-based expression vector that contains the β-lactamase gene and origin of DNA replication from pAT153, the SV40 origin of DNA replication and T-antigen coding sequences and a multicloning site adjacent to the SV40 late promoter (See FIG. 3). *E. coli* MC1061 (Casadabon, M. and S. Cohen, *J. Mol. Biol.* 138: 179–207 (1980)) was transformed with the annealed cDNA-plasmid mixture using a high efficiency transformation procedure that yields $10^8$ transformants per μg of vector DNA. Forty-six independent pools containing approximately 2,000–3,000 ampicillin-resistant clones were stored in 10% glycerol at –70° C.

Screening of cDNA Clones

For screening by colony hybridization, approximately 4,000 bacterial colonies from each pool were grown on agar plates (containing 40 μg ml$^{-1}$ ampicillin), transferred to nitrocellulose filter disks and plasmid DNA amplified by incubation of the filter on agar plates containing 200 μg ml$^{-1}$ chloramphenicol (Hanahan, D. & M. Meselson *Gene* 10: 63–67 (1980)). After regrowth of colonies on the original plate, a second nitrocellulose filter was prepared. The master plate was regrown a second time and then stored at 4° C. Plasmid DNA was released from the bacterial colonies and fixed to the nitrocellulose filters (Nicola N. & D. Metcalf, *J. cell Physiol.* 112: 257–264 (1982)). Before hybridization, filters were incubated for several hours at 37° C. in 6xSSC (SSC=0.15M NaCl, 0.015M sodium citrate), 0.2% Ficoll, 0.2% polyvinyl-pyrrollidone (PVP), 0.2% bovine serum albumin (BSA) containing 50 μg ml$^{-1}$ of denatured salmon sperm DNA and 10 μg ml$^{-1}$ of denatured *E. coli* DNA. Hybridization was in the same solution, containing 0.1% NP40, at 37° C. for about 18 hours. The synthetic oligonucleotide probes described above were radioactively labelled using [γ-$^{32}$p] ATP and polynucleotide kinase and each was present in the hybridization reaction at 1.5 nm ml$^{-1}$. After hybridization, filters were extensively washed in 6xSSC, 0.1% SDS at 42° C. and then autoradiographed. Colonies positive on duplicate filters were picked and rescreened at low density as before.

Screening of ~100,000 cDNA clones yielded 22 positives, of which two (pGM37 and pGM38) hybridized separately with probe 1 and with a mixture of 3 plus 4 and were therefore strong candidates to contain sequences coding for GM-CSF.

EXAMPLE II

This Example demonstrates the ability of pGM38 to select mRNA capable of directing the synthesis of GM-CSF.

Assays for GM-CSF

GM-CSF mRNA was identified by translation in Xenopus oocytes and the culture medium assayed for ability to stimulate granulocyte/macrophage proliferation in three microculture system: (1) liquid cultures containing purified fetal liver haematopoietic progenitor cells, which respond directly to all four colony stimulating factors (Burgess, A. W., et al., Blood 60: 1219–23 (1982)); (2) micro-agar cultures containing bone marrow cells, in which the formation of morphologically identifiable granulocyte and macrophage colonies can be stimulated by all four colony stimulating factors; and (3) liquid cultures containing the factor-dependent mast cell line 32D C13, which responds to multi-CSF but not GM-CSF. From this set of assays, GM-CSF and multi-CSF can be unambiguously distinguished.

Detection of GM-CSF mRNA in Various Cells

Figure 4:
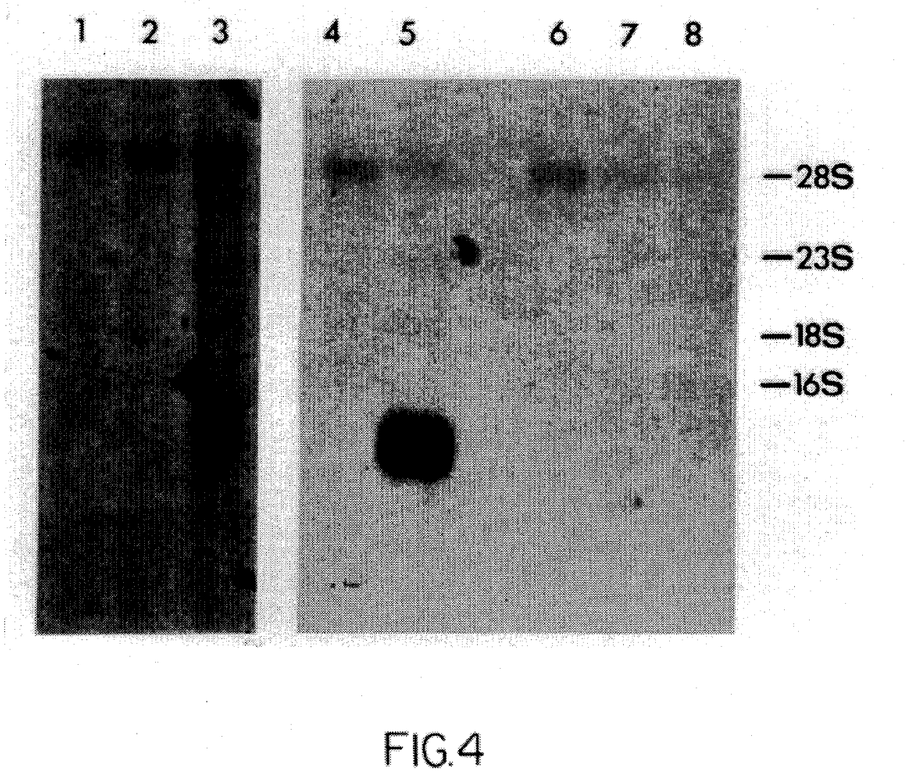
FIG. 4 illustrates the detection of GM-CSF mRNA in various cells by hybridization with $^{32}$P-labelled DNA from pGM38.

Initially it was determined whether the abundance of transcripts corresponding to pGM38 in various cell types paralleled the ability of those cells to synthesize GM-CSF. Messenger RNA from mouse lung (which synthesizes GM-CSF) and from various cells which do not synthesize GM-CSF was fractionated on formaldehyde-agarose gels, transferred to nitrocellulose and hybridized with a probe derived from pGM38 as detailed below. FIG. 4 shows that this probe detected a low abundance transcript of about 1.2 kilobases (kb) in mRNA from mouse lung (lane 3), but not in mPNA from several randomly selected cell lines which do not synthesize GM-CSD, including the thymoma-derived cell line TIKAUT (lane 1) and the plasmacytoma P3 (lane 2). Furthermore, this probe failed to detect any transcript in mRNA from WEH1-3B D$^-$ (lane 6), RIII (lane$^{-7}$) and L cells (lane 8), which synthesize multi-CSF, G-CSF and M-CSF respectively. The very low abundance of the transcript corresponding to pGM38 in lung mRNA was surprising given the low frequency of pGM38-related cDNA clones in the lung cDNA library (~1 in 50,000).

As a more critical test of whether transcripts complementary to pGM38 correlated with GM-CSF production, a cloned T lymphocyte cell line (LB3) was used in which the synthesis of both GM-CSF and multi-CSF is induced by concanavalin A. FIG. 4 shows that the pGM38-drived probe detected an abundant mRNA in LB3 cells that had been stimulated with concanavalin A (lane 5) but failed to detect any transcript in mRNA from unstimulated LB3 cells (lane 4). As the probe used does not hybridize to the multi-CSF mRNA in WEH1-3B D$^-$ (lane 6), such is further evidence that pGM38 hybridized to the GM-CSF mRNA in LB3 cells.

The detection of GM-CSF mRNA in the various cells was accomplished as follows. 5 μg of poly (A) RNA from TIKAUT (lane 1), P3 (lane 2), mouse lung (lane 3), unstimulated LB3 (lane 4), concanavalin A-stimulated LB3 (lane 5), WEH13B D$^-$ (lane 6), RIII (lane 7) and L cells (lane 8) were electrophoresed on 1% formaldehyde/agarose gels, transferred to nitrocellulose and hybridized with a fragment of DNA spanning the entire insert of pGM38 $^{32}$P-labelled by nick-translation (Rigby, P. W. J., et al., *J. Mol. Biol.* 113: 237–251 (1977)). Hybridization was at 65° C. for 16 hours in 2xSSC, 0.1% SDS, 0.2% Ficoll, 0.2% PVP, 0.2% BSA containing 50 μg ml$^{-1}$ of denatured salmon sperm DNA. LB3 (formerly B3) is a cloned Thy-1$^+$, Lyt-2$^-$, MT4$^+$ T lymphocyte line derived from BALB/c anti-DBA/2 mixed leukocyte culture, and maintained by weekly passage with irradiated DBA/2 spleen cells (1,500 R) in the presence of interleukin-2. Concanavalin A-stimulated LB3 cells were prepared by culturing cells at 10$^6$ per ml with 5 μg ml$^{-1}$ concanavalin A in tissue culture medium with 5% fetal calf serum for 5 hours. The molecular weight markers used and their presumed molecular weights were: mammalian 28 and 18S rRNA (4,700 and 1,800 nucleotides) and *E. coli* 23 and 16S rRNA (2,904 and 1,541 nucleotides). A lower level of hybridization to residual 28S rRNA is evident after long autoradiographic exposure (tracks 1–3).

Hybrid Selection of GM-CSF mRNA and Translation in Xenopus Oocytes

Hybrid selection was performed essentially as described by Miller, J. S., et al. (*Meth. Enzym.* 101: 650–674 (1983)). pGM38 or vector (pJL3) DNA (5-ug aliquots) were bound to small squares of nitrocellulose and incubated with 1–2 μg aliquots of concanavalin A-stimulated LB3 mRNA in 50% formamide, 0.5M Tris-HCl pH 7.5, 0.75M NaCl, 0.002M EDTA, 0.4% SDS, 10 ug ml$^{-1}$ *E. coli* tRNA in a reaction volume of 30 ul at 37° C. for 16 hours. After incubation, filters were exhaustively washed in hybridization buffer at 37° C. and then in 10 mM Tris-HCl pH 7.5, 2 mM EDTA at 52° C. Bound RNA was eluted by boiling for 1 minute in 300 μl 10 mM Tris-HCl pH 7.5, 2 mM EDTA containing 1.5 ug of *E. coli* tRNA. RNA was precipitated by addition of sodium acetate and ethanol and chilling at −20° C. for 16 hours. After centrifugation, precipitated RNA was washed with cold 70% ethanol, dried and redissolved in 1.5 μl 1 mM Tris-HCl pH 7.5, 0.1 mM EDTA. For each RNA sample, groups of 30 Xenopus oocytes were injected with 50 nl of RNA per egg. Unfractionated LB3 mRNA was at 1 μg ml$^{-1}$ for injection and 50 nl was injected per egg. After incubation of injected oocytes for 4 days, oocyte culture medium was diluted 1:2 in medium containing 5% fetal calf serum, filtered and 5-μl volumes assayed in serial dilutions in 15-ul cultures containing 200 fluorescence-activated cell sorter fractionated 14 day CBA fetal liver progenitor cells for 200 32D C13 cells. Each point in FIG. 5 represents the mean cell count from duplicate cultures after 2 days of incubation.

Figure 5A:
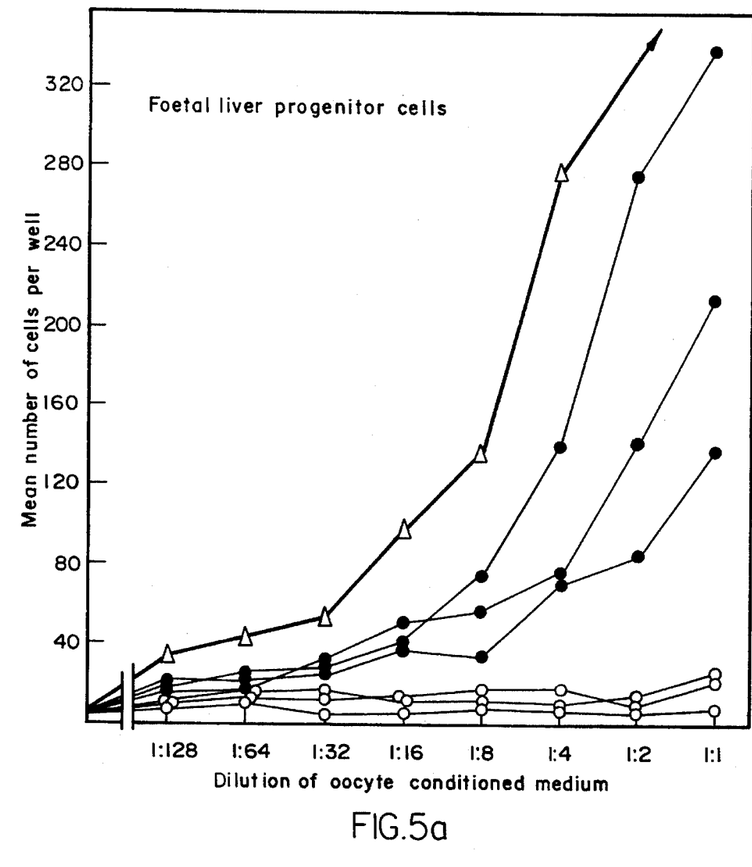
FIG. 5 illustrates the stimulation of cellular proliferation in suspension cultures of haematopoietic progenitor cells from fetal liver (upper panel) and multi-CSF-dependent 32D C12 cells (lower panel) by medium from mRNA-injected xenopus oocytes. Unfractionated LB3 mRNA is indicated by heavy lines o—o, mRNA selected by hybridization to pGM38 DNA; o—o, that selected by vector DNA alone; the three separate curves represent triplicate experiments.
Figure 5B:
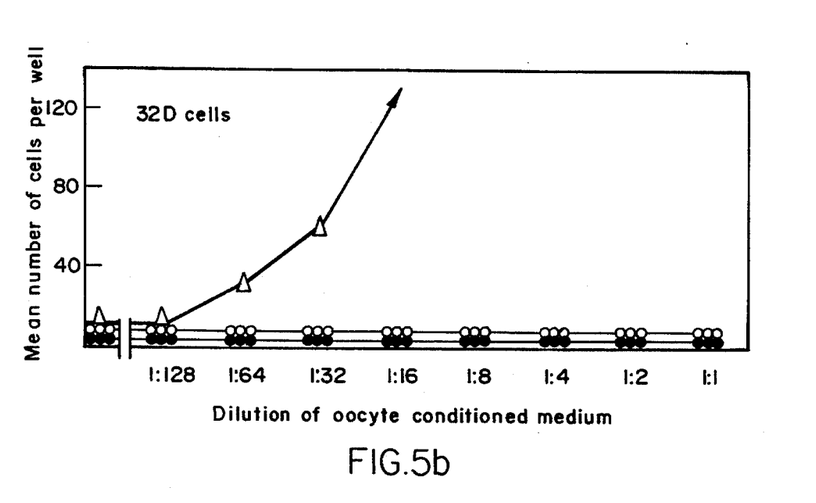
Figure 6:
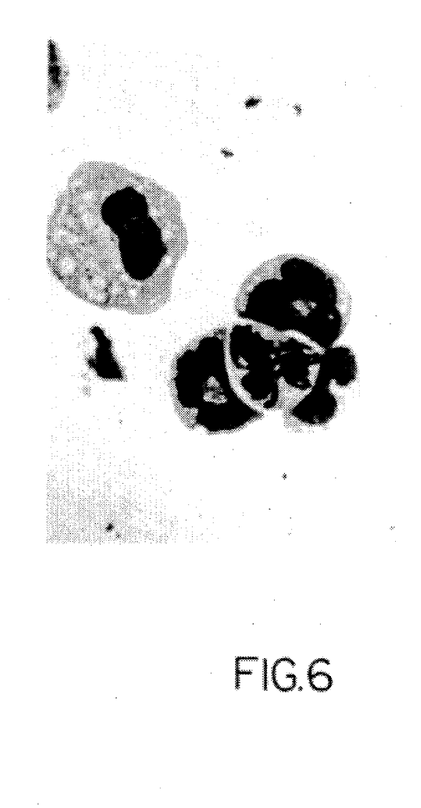
FIG. 6 is a photomicrograph of a four-day suspension culture of purified fetal liver haematopoietic progenitor cells after stimulation by medium from oocytes injected with pGM38-selected mRNA from LB3cells. Mitotic activity and the production of maturing granulocytes and macrophages can be noted.

Initially, a test was performed to determine whether pGM38 DNA could select GM-CSF mRNA from mouse lung RNA. After injection of unfractionated lung mRNA or mRNA selected by hybridization to pGM38 DNA into Xenopus oocytes, very low levels of CSF activity could be detected in the culture media, a finding that was anticipated from the very low abundance of mRNA corresponding to pGM38 in mouse lung (FIG. 4). By contrast, mRNA from concanavalin A-stimulated LB3 cells (which synthesize both GM- and multi-CSF) is rich in mRNA corresponding to pGM38 (FIG. 4) and on injection into Xenopus oocytes, reproducibly directed the synthesis of high levels of material stimulating the proliferation of fetal liver and 32D C13 cells (FIG. 5). Triplicate filters containing either pGM38 or vector DNAs were therefore challenged with concanavalin A-stimulated LB3 mRNA in a hybrid-selection experiment as described above. FIG. 5 shows that medium from oocytes injected with mRNA selected by pGM38 DNA strongly stimulated fetal progenitor cell proliferation with the development of maturing granulocytes and macrophages (FIG. 6). These oocyte-conditioned media also stimulated typical granulocyte-macrophage colony formation in micro-agar cultures (18% granulocyte, 53% mixed granulocyte-macrophage and 29% macrophage colonies). In neither assay was there evidence that these oocyte-conditioned media stimulated the proliferation of erythroid, megakaryocytic or eosinophilic cells, hence the active factor appeared to be GM-CSF rather than multi-CSF. In confirmation of this conclusion, these oocyte-conditioned media were found to be incapable of stimulating proliferation of 32D C13 cells (FIG. 5). Vector DNA alone failed to select mRNA corresponding to GM-CSF or multi-CSF (FIG. 5a, b).

Taken together, these data demonstrate that pGM38 DNA can specifically select a mRNA encoding a factor with the unique biological characteristics of GM-CSF from a mixture containing both GM-CSF and multi-CSF mRNAs.

EXAMPLE III

This Example provides the nucleotide sequence of GM-CSF gene.

Nucleotide sequence analysis of the cDNA portion of pGM37 and pGM38 revealed that these two clones, which contain sequences complementary to overlapping portions of the same mRNA contain the putative GM-CSF mRNA sequence. The relationship between the cDNA portion of the two clones and the mRNA is shown in FIG. 2a. The nucleotide sequence given in FIG. 2b is a composite derived from both clones. A stretch of 20 adenosine residues, corresponding to the poly(A) tail of the mRNA, preceded by the hexanucleotide AATAAA (found toward the 3' terminus of most eukaryotic mRNAs) is present at one end of pGM38. This allowed orientation of the sequences of the cDNA clones with that of the mRNA.

The sequences presented in FIG. 2b contains a single large open reading frame of 354 nucleotides; the amino acid sequence predicted by this region is presented from the first residue of the mature protein and is given above the nucleotide sequence. From residues 2 to 29, the amino acid sequence is identical (but for four residues) with the partial $NH_2$-terminal amino acid sequence for GM-CSF, which is shown above that predicted by the cDNA. Of the four discrepancies, two of the residues (20 and 24) had been only tentatively assigned in the sequence of the protein. The first residue on the mature peptide, which could not be determined in the protein sequence, is predicted by the nucleotide sequence to be isoleucine. The primary structure of the protein deduced from the nucleotide sequence has a molecular weight of 13,500, which is in good agreement with the apparent molecular weight of 16,800 for GM-CSF extensively deglycosylated with endoglycosidase F. Two potential N-glycosylation sites (Asn-X-Thr) which occur within the predicted amino acid sequence, are indicated in FIG. 2b by asterisks.

pGM37 extends 20 nucleotides 5' to the first position presented in FIG. 2b and does not contain an initiation codon; several hydrophobic amino acids are contained within this region (not shown), a characteristic of signal peptides of secreted proteins. The size of the GM-CSF mRNA is ~1,200 nucleotides (FIG. 4), of which ~150 nucleotides are probably contributed by the poly(A) tail. The 3' untranslated region is 319 nucleotides and the region encoding the mature protein 354 nucleotides (FIG. 2b). Thus some 350 nucleotides remain for the putative ($NH_2$-terminal signal peptide an the 5' untranslated region.

There are three discrepancies between the nucleotide sequence derived from the two cDNA clones (positions 237, 346 and 507), one of which (position 346) causes an amino acid sequence ambiguity (Gly or Ser at amino acid residue 116). As the mice (C57BL/6) from which the cDNA clones were isolated are highly inbred and hence should be homozygous at the GM-CSF locus, and as there appears to be only one gene encoding GM-CSF in the mouse germ line, it is likely that these three sequences ambiguities reflect artefacts created during cDNA synthesis, and indeed reverse transcriptase has an error frequency on synthetic polynucleotides of approximately one in 600 nucleotides.

Standard methods were employed for the determination of the sequence presented in FIG. 2. Briefly, the DNA fragments subcloned in M13 vectors were sequenced by the chain-termination method using dideoxy-nucleoside trisphosphates (Sanger, F. et al., *Proc. Nat'l. Acad. Sci. USA* 74: 5462–67 (1977)). Sequencing reactions were electrophoresed on thermostatically controlled 0.2 mm thick, 8% (w:v) polyacrylamide gels. As mentioned above in reference to FIG. 2, the sequence of the mRNA-synonymous strand is listed 5' to 3' with the predicted amino acid sequence of GM-CSF given above; numbers at the ends of lines indicated the position of the final residue (amino acid or nucleotide) on that line. The partial amino acid sequence determined for GM-CSF is indicated above the sequence derived from the clones; at positions where there is no discordance between the two, dashes are given. The first amino acid residue, determined by analysis of the protein, could not be assigned, and is indicated by a question mark. Potential N-glycosylation sites are indicated with asterisks, and the putative polyadenylation signal is underlined.

EXAMPLE IV

This Example demonstrates that GM-CSF is encoded by a unique gene.

As there are known to be multiple molecular forms of GM-CSF isolated from various mouse organs, how many genes the GM-CSF cDNA could detect in the murine genome was tested. BALB/c embryo or C57BL/6 liver DNA digested with various restriction endonucleases was fractionated on agarose gels, transferred to nitrocellulose and hybridized with a fragment containing the entire cDNA insert in pGM38. In both mouse strains, a single EcoRI fragment (FIG. 7, lanes 1,2), a single PstI fragment (lanes 3, 4) and a single BamHI fragment (not shown) were detected. Since the PstI fragment is only 2.5 kb in length it is unlikely that this fragment could accommodate more than one gene. It is concluded therefore that there is only one gene encoding the lung-type GM-CSF in the mouse germ line, barring the unlikely possibility that two (or more) genes are flanked by identically positioned EcoRI, PstI and BamHI restriction sites.

Figure 7:
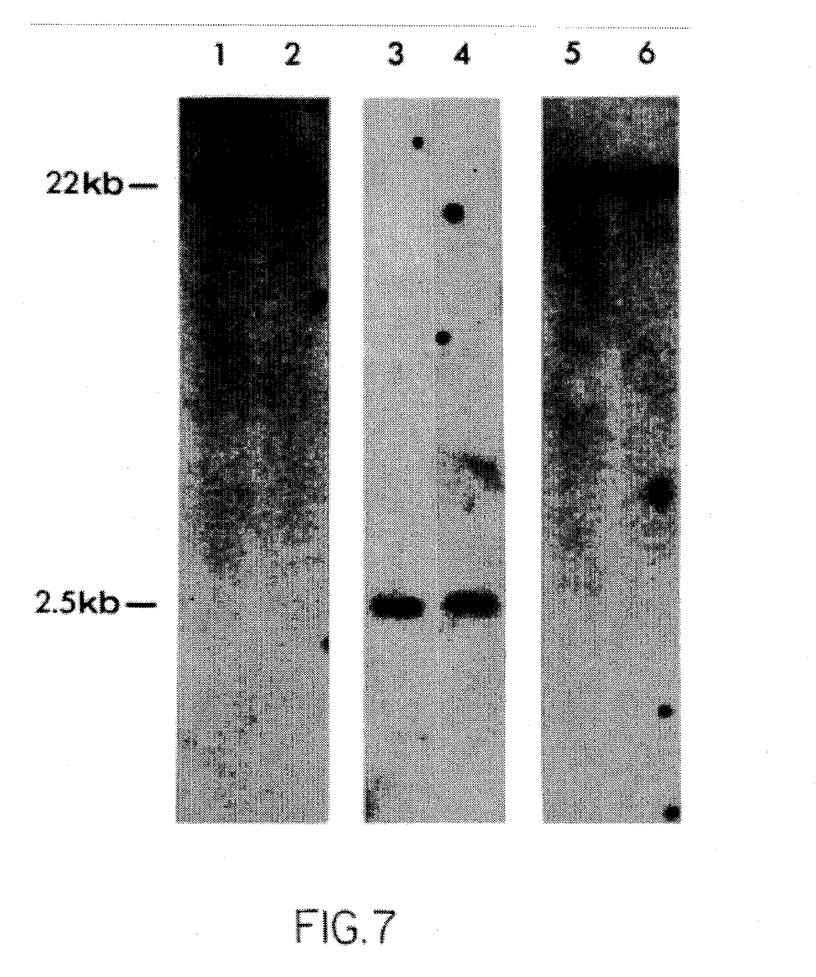
FIG. 7 illustrates the detection of the GM-CSF gene from Eco R1 or Pst I digested DNA hybridized with $^{32}$P-labelled DNA from pGM38.

FIG. 7 also reveals that the GM-CSF gene is contained within the same EcoRI fragment in DNA from concanavalin A-stimulated LB3 cells (lane 6) as in embryo DNA (lane 5). No additional bands were evident in LB3 DNA nor was the intensity of hybridization different from that of embryo DNA, from which it is inferred that there are no alterations in the copy number or gross changes in the context of the GM-CSF gene in cells which synthesize large quantities of GM-CSF.

What is claimed is:

1. A method of producing mammalian GM-CSF comprising culturing a host cell transformed by an expression vector which comprises a promoter which functions in said host and a DNA which hybridizes to the plasmid pGM37 or pGM38 wherein said DNA encodes mammalian GM-CSF in said host and wherein said DNA is in orientation with said promoter such that in said host cell the mammalian GM-CSF DNA is expressed.

2. The method of claim 1 wherein said GM-CSF protein is recovered in substantially pure form.

3. A method of producing mammalian GM-CSF comprising culturing a host cell transformed by an expression vector which comprises a promoter which functions in said host and a DNA which hybridizes to the complement of the nucleotide sequence ATAATTGTTACCCGGCCTTGGAAGCATG-
TAGAGGCCATCAAAGAAGCCCTAAACCTCCTG
GATGACATGCCTGTCACGTTGAATGAA-
GAGGTAGAAGTCGTCTCTAACGAGT-
TCTCCTTC AAGAAGCTAACATGTGTGCAGAC-
CCGCCTGAAGATATTCGAGCAGGGTCTACGGG-
GCAAT TTCACCAAACTCAAGGGCGCCTTGAA-
CATGACAGCCAGCTACTACCAGACAT-
ACTGYCCC CCAACTCCGGAAACGGACTGT-
GAAACACAAGTTACCACCTATGCGGATTTCAT-
AGACAGC CTTAAAACCTTTCTGACTGATATC-
CCCTTTGAATGCAAAAAACCARGC-
CAAAAATGAGGA AGCCCAGGCCAGCTCT-
GAATCCAGCTTCTCAGACTGCTGCTTTTGTGC-
CTGCGTAATGAG CCAAGAACTTGGAATTTCT-
GCCTTAAAGGGACCAAGAGATGTGGCA-
CAGCCACAGTTGGA AGGCAGTATAGCCCTCT-
GAAAACGCTRACTCAGCTTGGACAGCGGAAG-
ACAAACGAGAGA TATTTTCTACTGATAGGGAC-
CATTATATTTATTTATATATT-
TATATTTTTTAAATATTAT TTATTTATTTATT-
TATTTTTGCAACTCTATTTATTGAGAATGTCTTA-
CCAGAATAATAAA TTATTAAAACTT-
TAAAAAAAAAAAAAAAAAAAA;

wherein Y is C or T; wherein R is A or G; and wherein said DNA encodes mammalian GM-CSF in said host, and wherein said DNA is in orientation with said promoter such that in said host cell the mammalian GM-CSF DNA is expressed.

4. The method of claim 3 wherein GM-CSF is recovered in substantially pure form.

5. The method according to claim 3 wherein said DNA comprises the sequence:

ATAATTGTTACCCGGCCTTGGAAGCATG-
TAGAGGCCATCAAAGAAGCCCTAAACCTCCTG
GATGACATGCCTGTCACGTTGAATGAA-
GAGGTAGAAGTCGTCTCTAACGACT-
TCTCCTTC AAGAAGCTAACATGTGTGCAGAC-
CCGCCTGAAGATATTCGAGCAGGGTCTACGGG-
GCAAT TTCACCAAACTCAAGGGCGCCTTGAA-
CATGACAGCCAGCTACTACCAGACAT-
ACTGyCCC CCAACTCCGGAAACGGACTGT-
GAAACACAAGTTACCACCTATGCGGATTTCAT-
AGACAGC CTTAAAACCTTTCTGACTGATATC-
CCCTTTGAATGCAAAAAACCARGC-
CAAAAATGA;

wherein Y is C or T and wherein R is A or G.

6. A method of producing mammalian GM-CSF comprising transforming a host cell by an expression vector which comprises a promoter which functions in said host and a DNA which hybridizes to the complement of the nucleotide sequence ATAATTGTTACCCGGCCTTGGAAGCATG-
TAGAGGCCATCAAAGAAGCCCTAAACCTCCTG
GATGACATGCCTGTCACGTTGAATGAA-
GAGGTAGAAGTCGTCTCTAACGAGT-
TCTCCTTC AAGAAGCTAACATGTGTGCAGAC-
CCGCCTGAAGATATTCGAGCAGGGTCTACGGG-
GCAAT TTCACCAAACTCAAGGGCGCCTTGAA-
CATGACAGCCAGCTACTACCAGACAT-
ACTGYCCC CCAACTCCGGAAACGGACTGT-
GAAACACAAGTTACCACCTATGCGGATTTCAT-
AGACAGC CTTAAAACCTTTCTGACTGATATC-
CCCTTTGAATGCAAAAAACCARGC-
CAAAAATGAGGA AGCCCAGGCCAGCTCT-
GAATCCAGCTTCTCAGACTGCTGCTTTTGTGC-
CTGCGTAATGAG CCAAGAACTTGGAATTTCT-
GCCTTAAAGGGACCAAGAGATGTGGCA-
CAGCCACAGTTGGA AGGCAGTATAGCCCTCT-
GAAAACGCTRACTCAGCTTGGACAGCGGAAG-
ACAAACGAGAGA TATTTTCTACTGATAGGGAC-
CATTATATTTATTTATATATT-
TATATTTTTTAAATATTAT TTATTTATTTATT-
TATTTTTGCAACTCTATTTATTGAGAATGTCTTA-
CCAGAATAATAAA TTATTAAAACTT-
TAAAAAAAAAAAAAAAAAAAA;

wherein Y is C or T; wherein R is A or G; and wherein said DNA encodes mammalian GM-CSF in said host, and wherein said DNA is in orientation with said promoter such that in said host cell the mammalian GM-CS DNA is expressed.

7. A host cell transformed with plasmid pGM37.

8. The host cell of claim 7 having the identifying characteristic of ATCC 53032.

9. A host cell transformed with plasmid pGM38.

10. The host cell of claim 9 having the identifying characteristic of ATCC 53036.

11. A cloning vector comprising a DNA sequence which encodes GM-CSF.

12. The vector according to claim 11 wherein said vector is plasmid pGM37.

13. The vector according to claim 11 wherein said vector is plasmid pGM38.

14. A host cell transformed by the vector of claim 11.

15. The vector according to claim 11 wherein said sequence is:

ATAATTGTTACCCGGCCTTGGAAGCATG-
TAGAGGCCATCAAAGAAGCCCTAAACCTCCTG
GATGACATGCCTGTCACGTTGAATGAA-
GAGGTAGAAGTCGTCTCTAACGAGT-
TCTCCTTC AAGAAGCTAACATGTGTGCAGAC-
CCGCCTGAAGATATTCGAGCAGGGTCTACGGG-
GCAAT TTCACCAAACTCAAGGGCGCCTTGAA-
CATGACAGCCAGCTACTACCAGACAT-
ACTGYCCC CCAACTCCGGAAACGGACTGT-
GAAACACAAGTTACCACCTATGCGGATTTCAT-
AGACAGC CTTAAAACCTTTCTGACTGATATC-
CCCTTTGAATGCAAAAAACCARGC-
CAAAAATGAGGA AGCCCAGGCCAGCTCT-

GAATCCAGCTTCTCAGACTGCTGCTTTTGTGC-
CTGCGTAATGAG CCAAGAACTTGGAATTTCT-
GCCTTAAAGGGACCAAGAGATGTGGCA-
CAGCCACAGTTGGA AGGCAGTATAGCCCTCT-
GAAAACGCTRACTCAGCTTGGACAGCGGAAG-
ACAAACGAGAGA TATTTTCTACTGATAGGGAC-
CATTATATTTATTTATATATT-
TATATTTTTAAATATTAT TTATTTATTTATT-
TATTTTTGCAACTCTATTTATTGAGAATGTCTTA-
CCAGAATAATAAA TTATTAAAACTT-
TAAAAAAAAAAAAAAAAAAAA; and wherein Y is C or T and wherein R is A or G.

16. The vector according to claim 11 wherein said sequence is:

ATAATTGTTACCCGGCCTTGGAAGCATG-
TAGAGGCCATCAAAGAAGCCCTAAACCTCCTG
GATGACATGCCTGTCACGTTGAATGAA-
GAGGTAGAAGTCGTCTCTAACGACT-
TCTCCTTC AAGAAGCTAACATGTGTGCAGAC-
CCGCCTGAAGATATTCGAGCAGGGTCTACGGG-
CCAAT TTCACCAAACTCAAGGGCGCCTTGAA-
CATGACAGCCAGCTACTACCAGACAT-
ACTGYCCC CCAACTCCGGAAACGGACTGT-
GAAACACAAGTTACCACCTATGCGGATTTCAT-
AGACAGC CTTAAAACCTTTCTGACTGATATC-
CCCTTTGAATGCAAAAAACCARGC-
CAAAAATGA;

wherein Y is C or T and wherein R is A or G.

17. An isolated DNA encoding mammalian granulocyte-macrophage colony stimulating factor (GM-CSF).

18. The DNA according to claim 17 wherein mammalian is murine.

19. The DNA according to claim 17 wherein said DNA is cDNA.

20. A method of producing the DNA coding for the GM-CSF of claim 17 comprising the steps of:

(a) isolating mRNA from a cell which produces GM-CSF;

(b) synthesizing duplex DNA copies of said source mRNA;

(c) cloning said DNA copies;

(d) providing synthetic GM-CSF probes to hybridize with the DNA of step (b);

(e) screening clones harboring the DNA copies of step (b) by colony hybridization with the probes of step (d);

(f) and recovering the clones which hybridize with said probes.

21. The method according to claim 20 wherein said source of mRNA is lung mRNA isolated from C57 BL/6 mice injected with bacterial endotoxin.

22. The product of the process of claim 20.

23. The DNA according to claim 17 having the following DNA sequence in a 5' to 3' direction ATAATTGTTACCCGGCCTTGGAAGCATG-
TAGAGGCCATCAAAGAAGCCCTAAACCTCCTG
GATGACATGCCTGTCACGTTGAATGAA-
GAGGTAGAAGTCGTCTCTAACGAGT-
TCTCCTTC AAGAAGCTAACATGTGTGCAGAC-
CCGCCTGAAGATATTCGAGCAGGGTCTACGGG-
GCAAT TTCACCAAACTCAAGGGCGCCTTGAA-
CATGACAGCCAGCTACTACCAGACAT-
ACTGYCCC CCAACTCCGGAAACGGACTGT-
GAAACACAAGTTACCACCTATGCGGATTTCAT-
AGACAGC CTTAAAACCTTTCTGACTGATATC-
CCCTTTGAATGCAAAAAACCARGC-
CAAAAATGAGGA AGCCCAGGCCAGCTCT-
GAATCCAGCTTCTCAGACTGCTGCTTTTGTGC-
CTGCGTAATGAG CCAAGAACTTGGAATTTCT-
GCCTTAAAGGGACCAAGAGATGTGGCA-
CAGCCACAGTTGGA AGGCAGTATAGCCCTCT-
GAAAACGCTRACTCAGCTTGGACAGCGGAAG-
ACAAACGAGAGA TATTTTCTACTGATAGGGAC-
CATTATATTTATTTATATATT-
TATATTTTTAAATATTAT TTATTTATTTATT-
TATTTTTGCAACTCTATTTATTGAGAATGTCTTA-
CCAGAATAATAAA TTATTAAAACTT-
TAAAAAAAAAAAAAAAAAAAA;

wherein Y is C or T and wherein R is A or G.

24. The DNA according to claim 23 has the following DNA sequence in a 5' to 3' direction ATAATTGTTACCCGGCCTTGGAAGCATG-
TAGAGGCCATCAAAGAAGCCCTAAACCTCCTG
GATGACATGCCTGTCACGTTGAATGAA-
GAGGTAGAAGTCGTCTCTAACGACT-
TCTCCTTC AAGAAGCTAACATGTGTGCAGAC-
CCGCCTGAAGATATTCGAGCAGGGTCTACGGG-
GCAAT TTCACCAAACTCAAGGGCGCCTTGAA-
CATGACAGCCAGCTACTACCAGACAT-
ACTGYCCC CCAACTCCGGAAACGGACTGT-
GAAACACAAGTTACCACCTATGCGGATTTCAT-
AGACAGC CTTAAAACCTTTCTGACTGATATC-
CCCTTTGAATGCAAAAAACCARGC-
CAAAAATGA;

wherein Y is C or T and wherein R is A or G.

25. The method according to claim 20 wherein said probes are selected from the group consisting of:

3' ACCTTYGTRCAXCTYCG 5';

3' ACCTTYACRCAWCTYCG 5';

3' CTYCGRTAZTTYCTYCG 5';

3' CTYCGYTAZTTYCTYCG 5';

ATAATTGTTACCCGGCCTTGGAAGCATG-
TAGAGGCCATCAAAGAAGCCCTAAACCTCCTG
GATGACATGCCTGTCACGTTGAATGAA-
GAGGTAGAAGTCGTCTCTAACGAGT-
TCTCCTTC AAGAAGCTAACATGTGTGCAGAC-
CCGCCTGAAGATATTCGAGCAGGGTCTACGGG-
GCAAT TTCACCAAACTCAAGGGCGCCTTGAA-
CATGACAGCCAGCTACTACCAGACAT-
ACTGYCCC CCAACTCCGGAAACGGACTGT-
GAAACACAAGTTACCACCTATGCGGATTTCAT-
AGACAGC CTTAAAACCTTTCTGACTGATATC-
CCCTTTGAATGCAAAAAACCARGC-
CAAAAATGAGGA AGCCCAGGCCAGCTCT-
GAATCCAGCTTCTCAGACTGCTGCTTTTGTGC-
CTGCGTAATGAG CCAAGAACTTGGAATTTCT-
GCCTTAAAGGGACCAAGAGATGTGGCA-
CAGCCACAGTTGGA AGGCAGTATAGCCCTCT-
GAAAACGCTRACTCAGCTTGGACAGCGGAAG-
ACAAACGAGAGA TATTTTCTACTGATAGGGAC-
CATTATATTTATTTATATATT-
TATATTTTTAAATATTAT TTATTTATTTATT-
TATTTTTGCAACTCTATTTATTGAGAATGTCTTA-
CCAGAATAATAAA TTATTAAAACTT-
TAAAAAAAAAAAAAAAAAAAA; and ATAATTGTTACCCGGCCTTGGAAGCATG-
TAGAGGCCATCAAAGAAGCCCTAAACCTCCTG
GATGACATGCCTGTCACGTTGAATGAA-
GAGGTAGAAGTCGTCTCTAACGACT-
TCTCCTTC AAGAAGCTAACATGTGTGCAGAC-
CCGCCTGAAGATATTCGAGCAGGGTCTACGGG-
GCAAT TTCACCAAACTCAAGGGCGCCTTGAA-
CATGACAGCCAGCTACTACCAGACAT-
ACTGYCCC CCAACTCCGGAAACGGACTGT- GAAACACAAGTTACCACCTATGCGGATTTCATAGACAGC CTTAAAACCTTTCTGACTGATATCCCCTTTGAATGCAAAAAACCARGCCAAAAATGA;

wherein R is A or G; W is A, G, T or C; X is C, T, A or G; Y is C or T and Z is A, G or T.

26. An isolated DNA which hybridizes to the plasmid pGM37 wherein said DNA encodes mammalian GM-CSF.

27. An isolated DNA which hybridizes to the plasmid pGM38 wherein said DNA encodes mammalian GM-CSF.

28. An isolated DNA which hybridizes to the complement of the nucleotide sequence ATAATTGTTACCCGGCCTTGGAAGCATGTAGAGGCCATCAAAGAAGCCCTAAACCTCCTGGATGACATGCCTGTCACGTTGAATGAAGAGGTAGAAGTCGTCTCTAACGAGTTCTCCTTC AAGAAGCTAACATGTGTGCAGACCCGCCTGAAGATATTCGAGCAGGGTCTACGGGGCAAT TTCACCAAACTCAAGGGCGCCTTGAACATGACAGCCAGCTACTACCAGACATACTGYCCC CCAACTCCGGAAACGGACTGTGAAACACAAGTTACCACCTATGCGGATTTCATAGACAGC CTTAAAACCTTTCTGACTGATATCCCCTTTGAATGCAAAAAACCARGCCAAAAATGAGGA AGCCCAGGCCAGCTCTGAATCCAGCTTCTCAGACTGCTGCTTTTGTGCCTGCGTAATGAG CCAAGAACTTGGAATTTCTGCCTTAAAGGGACCAAGAGATGTGGCACAGCCACAGTTGGA AGGCAGTATAGCCCTCTGAAAACGCTRACTCAGCTTGGACAGCGGAAGACAAACGAGAGA TATTTCTACTGATAGGGACCATTATATTTATTTATATATTTATATTTTTTAAATATTAT TTATTTATTTATTTATTTTTGCAACTCTATTTATTGAGAATGTCTTACCAGAATAATAAA TTATTAAAACTTTAAAAAAAAAAAAAAAAAAAA;

wherein Y is C or T; wherein R is A or G; and wherein said DNA encodes mammalian GM-CSF.

29. A vector comprising the DNA of any one of claims 28, 26 and 27.

30. A host cell transformed with the vector of claim 29.

31. A method for stimulating the production of granulocytes and macrophages comprising contacting the respective progenitor cells of said granulocytes and macrophages with a stimulating effective amount of an isolated and purified mammalian granulocyte-macrophage colony stimulating factor.

* * * * *